(12) United States Patent
Sun et al.

(10) Patent No.: US 12,430,799 B2
(45) Date of Patent: Sep. 30, 2025

(54) CALIBRATION OF TEMPERATURE MEASUREMENT SYSTEM WITH THERMAL SENSOR AND IMAGE SENSOR

(71) Applicant: PIXART IMAGING INC., Hsin-Chu County (TW)

(72) Inventors: Chih-Ming Sun, Hsin-Chu County (TW); Po-Wei Yu, Hsin-Chu County (TW); Yen-Chang Chu, Hsin-Chu County (TW)

(73) Assignee: PIXART IMAGING INC., Hsin-Chu County (TW)

( * ) Notice: Subject to any disclaimer, the term of this patent is extended or adjusted under 35 U.S.C. 154(b) by 937 days.

(21) Appl. No.: 17/567,184

(22) Filed: Jan. 3, 2022

(65) Prior Publication Data

US 2022/0122293 A1 Apr. 21, 2022

Related U.S. Application Data

(63) Continuation-in-part of application No. 17/385,046, filed on Jul. 26, 2021.

(60) Provisional application No. 63/071,383, filed on Aug. 28, 2020.

(51) Int. Cl.
| | |
|---|---|
| *G06T 7/80* | (2017.01) |
| *A61B 5/01* | (2006.01) |
| *G01J 5/00* | (2022.01) |
| *G01J 5/80* | (2022.01) |
| *G06T 7/30* | (2017.01) |
| *H04N 23/90* | (2023.01) |

(52) U.S. Cl.
CPC .................. *G06T 7/80* (2017.01); *A61B 5/01* (2013.01); *G01J 5/80* (2022.01); *G06T 7/30* (2017.01); *H04N 23/90* (2023.01); *A61B 2560/0223* (2013.01); *A61B 2562/0271* (2013.01); *G01J 2005/0077* (2013.01); *G06T 2207/10048* (2013.01); *G06T 2207/30201* (2013.01)

(58) Field of Classification Search
CPC ...................................................... G06T 7/80
See application file for complete search history.

(56) References Cited

U.S. PATENT DOCUMENTS

| | | |
|---|---|---|
| 2,651,237 A | 9/1953 | Garutso |
| 4,998,125 A | 3/1991 | Watanabe et al. |
| 5,687,408 A | 11/1997 | Park |
| 5,819,007 A | 10/1998 | Elghazzawi |
| 2003/0020002 A1 | 1/2003 | Lee |
| 2004/0254472 A1 | 12/2004 | McQuilkin |
| 2005/0017946 A1 | 1/2005 | Park |
| 2005/0146641 A1 | 7/2005 | Cheng |

(Continued)

FOREIGN PATENT DOCUMENTS

| | | |
|---|---|---|
| CN | 102176742 A | 9/2011 |
| CN | 103839218 A | 6/2014 |

(Continued)

*Primary Examiner* — Carolyn Fin
(74) *Attorney, Agent, or Firm* — HAUPTMAN HAM, LLP

(57) ABSTRACT

There is provided a temperature measurement system including an image sensor, a thermal sensor and a processor. The image sensor captures an image frame. The thermal sensor captures a thermal image. The processor calibrates measured temperatures of the thermal sensor and calibrates offset pixels between the image frame and the thermal image corresponding to different operating distances.

18 Claims, 14 Drawing Sheets

(56) References Cited

U.S. PATENT DOCUMENTS

| | | | |
|---|---|---|---|
| 2007/0153871 A1 | 7/2007 | Fraden | |
| 2007/0176213 A1 | 8/2007 | Oda | |
| 2008/0278608 A1 | 11/2008 | Kim et al. | |
| 2010/0110282 A1 | 5/2010 | Lan et al. | |
| 2013/0230074 A1 | 9/2013 | Shin | |
| 2014/0092939 A1 | 4/2014 | Chang et al. | |
| 2017/0209303 A1 | 7/2017 | Al-Anzi | |
| 2018/0092549 A1 | 4/2018 | Tzvieli et al. | |
| 2019/0195694 A1 | 6/2019 | Tang et al. | |
| 2020/0068110 A1* | 2/2020 | Guo | G01B 11/24 |
| 2021/0295517 A1* | 9/2021 | Parrish | G01J 5/0846 |
| 2021/0343005 A1 | 11/2021 | Kuybeda et al. | |
| 2021/0393139 A1 | 12/2021 | Manneschi et al. | |
| 2021/0404877 A1 | 12/2021 | Lee et al. | |

FOREIGN PATENT DOCUMENTS

| | | |
|---|---|---|
| CN | 111458039 A | 7/2020 |
| CN | 111537074 A | 8/2020 |
| JP | H01-289390 A | 11/1989 |
| JP | 2011159681 A | 8/2011 |

* cited by examiner

CALIBRATION OF TEMPERATURE MEASUREMENT SYSTEM WITH THERMAL SENSOR AND IMAGE SENSOR

CROSS REFERENCE TO RELATED APPLICATION

The present application is a continuation-in-part application of U.S. patent application Ser. No. 17/385,046 filed on, Jul. 26, 2021, which claims the priority benefit of U.S. Provisional Application Serial Number U.S. 63/071,383, filed on Aug. 28, 2020, the disclosures of which are hereby incorporated by reference herein in their entirety.

BACKGROUND

1. Field of the Disclosure

This disclosure generally relates to a temperature measurement system and, more particularly, to calibration of a temperature measurement system with a thermal sensor and an image sensor.

2. Description of the Related Art

It has become a new normal to arrange an auto forehead temperature measuring system at an entrance of the store and the building. However, different from the forehead thermometer, a distance between a measured person and the auto forehead temperature measuring system is not fixed, and a system's field of view generally covers environmental objects that could degrade the measurement accuracy. Furthermore, the fluctuated environmental temperature is also a parameter that could affect a measured temperature. Therefore, the current auto forehead temperature measuring system has a larger temperature deviation, and false alarm happens from time to time when the measured temperature is compared with a temperature threshold.

The present disclosure provides a temperature measurement system that can compensate or calibrate the temperature deviation caused by the distance from a measured person and by the environmental temperature fluctuation by using an image sensor. Furthermore, a position offset between two sensors that can degrade the accuracy of a measured temperature is also calibrated corresponding to different operating distances.

SUMMARY

The present disclosure provides a temperature measurement system that provides a calibration temperature based on a thermal image and an image frame.

The present disclosure further provides a temperature measurement system that compensates a position offset between a thermal sensor and an image sensor corresponding to different operating distances.

The present disclosure provides a temperature measurement system including an image sensor, a thermal sensor and a memory. The image sensor is configured to capture an image frame with a first field of view covering a predetermined heated region having a reference temperature. The thermal sensor is configured to capture a thermal image with a second field of view covering the predetermined heated region having the reference temperature. The memory is configured to record a calibration temperature which is a temperature difference between the reference temperature and a measured temperature of a first region of interest (ROI) associated with the predetermined heated region in the thermal image, wherein the first ROI overlaps at least a part of a second ROI associated with the predetermined heated region in the image frame while overlapping the image frame and the thermal image.

The present disclosure further provides a temperature measurement system including an image sensor, a thermal sensor, a memory and a processor. The image sensor is configured to capture an image frame. The thermal sensor is configured to capture a thermal image. The memory is configured to record a number of offset pixels between the image frame and the thermal image captured at a reference distance. The processor is coupled to the image sensor, the thermal sensor and the memory, and configured to calibrate the number of offset pixels according to a ratio of a difference between an operating distance and the reference distance with respect to the operating distance.

The present disclosure further provides a temperature measurement system including an image sensor, a thermal sensor and a memory. The image sensor is configured to capture an image frame with a first field of view covering a predetermined heated region having a reference temperature. The thermal sensor is configured to capture a thermal image with a second field of view covering the predetermined heated region having the reference temperature.

The memory, configured to record a calibration temperature which is a temperature difference between the reference temperature and a measured temperature of a first region of interest (ROI) associated with the predetermined heated region in the thermal image, wherein the first ROI overlaps at least a part of a second ROI associated with the predetermined heated region in the image frame while overlapping the image frame and the thermal image, and a number of offset pixels between the image frame and the thermal image captured at a reference distance.

The present disclosure further provides a temperature measurement system including an image sensor, a thermal sensor and a memory. The image sensor is configured to capture an image frame with a first field of view covering a predetermined heated region having a reference temperature. The thermal sensor is configured to capture a thermal image with a second field of view covering the predetermined heated region having the reference temperature.

The processor is configured to align a first region associated with the predetermined heated region in the thermal image with a second region associated with the predetermined heated region in the image frame.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

The forehead temperature measurement system of the present disclosure firstly determines a forehead region in an image frame captured by an image sensor using the image recognition technique, and then determines a measured forehead temperature according to a mapped region, corresponding to the forehead region, in a thermal image captured by a thermal sensor. Furthermore, the forehead temperature measurement system of the present disclosure further compensates or calibrates the measured forehead temperature according to an area of the forehead region so as to improve the measurement accuracy.

Figure 1:
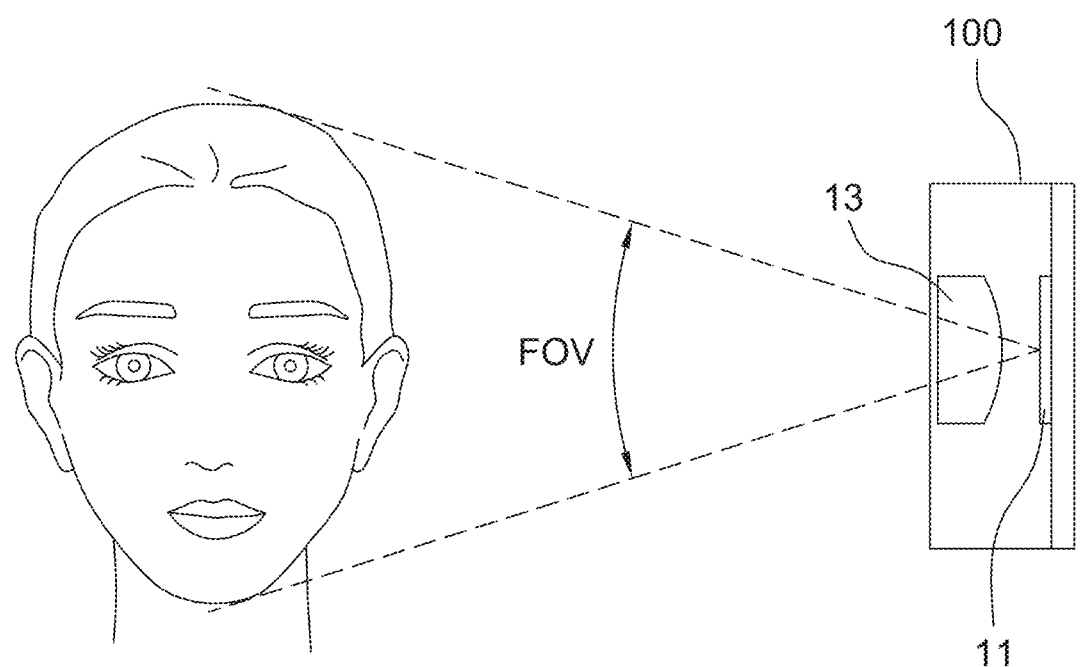
FIG. 1 is an operational schematic diagram of a forehead temperature measurement system according to one embodiment of the present disclosure.
Figure 2:
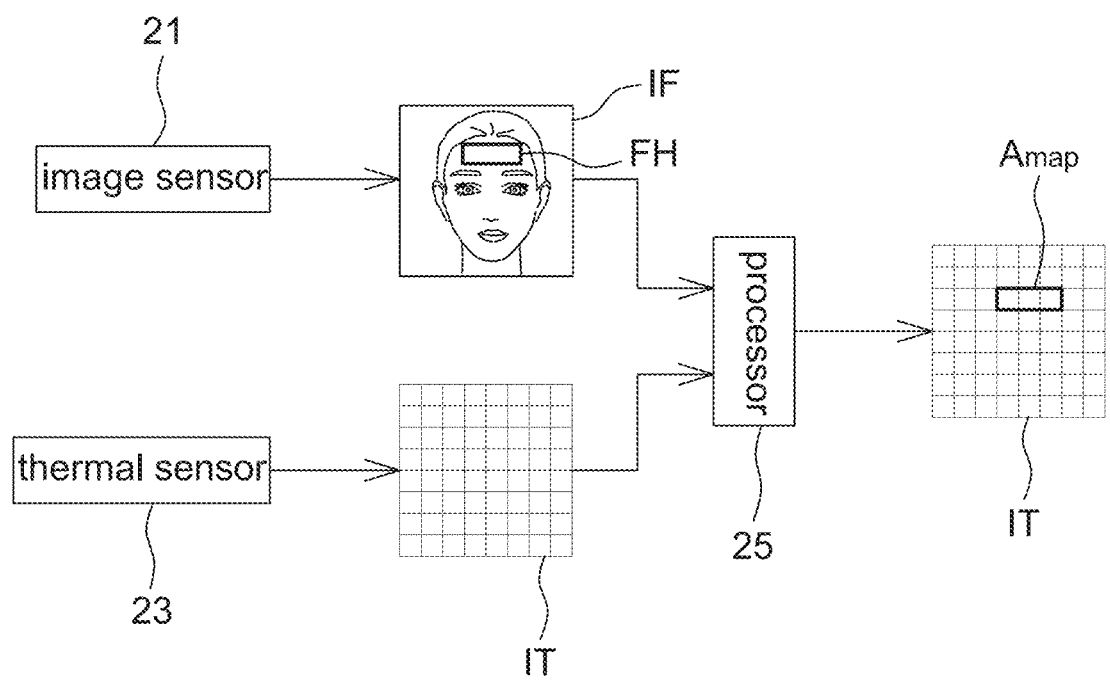
FIG. 2 is a schematic block diagram of a forehead temperature measurement system according to one embodiment of the present disclosure.

Please refer to FIGS. 1 and 2, FIG. 1 is an operational schematic diagram of a forehead temperature measurement system 100 according to one embodiment of the present disclosure, and FIG. 2 is a schematic block diagram of a forehead temperature measurement system 100 according to one embodiment of the present disclosure.

The forehead temperature measurement system 100 includes a sensing chip 11 and a lens 13, wherein the lens 13 is arranged at a side of the sensing chip 11 for receiving light so as to adjust the light path and field of view FOV.

The sensing chip 11 includes an image sensor 21, a thermal sensor 23 and a processor 25. The image sensor 21 and the thermal sensor 23 both receive optical energy via the lens 13. The sensing chip 11 is coupled to external devices via a substrate on which the sensing chip 11 is arranged.

The image sensor 21 (and 21' if included) is, for example, a CCD image sensor or a CMOS image sensor, and is used to output an image frame IF at a predetermined frequency. For example, FIG. 2 shows that the image frame IF contains a human face image. The thermal sensor 23 (and 23' if included) is a far infrared sensor, and is used to sense far infrared light generated by a human body to output, corresponding to capturing of the image frame IF, a thermal image IT.

In one aspect, the image sensor 21 and the thermal sensor 23 have an identical field of view FOV so as to receive optical energy from the same space, but the present disclosure is not limited thereto. In another aspect, the FOV of the image sensor 21 is larger than or smaller than that of the thermal sensor 23.

In one aspect, a pixel number of the image frame IF is higher than a pixel number of the thermal image IT. The image frame IF includes, for example, 240×240 pixels so as to contain enough details or features for the processor 25 to perform the image recognition, e.g., including face recognition and recognizing a forehead region of a face. The thermal image IT includes, for example, 8×8 pixels so as to detect temperatures of 64 points within the FOV.

The processor 25 is coupled to the image sensor 21 and the thermal sensor 23 to respectively receive the image frame IF and the thermal image IT. The processor 25 is, for example, a digital signal processor (DSP), an application specific integrated circuit (ASIC) or a field programmable gate array (FPGA), and implements functions thereof using hardware and/or firmware. Said functions include recognizing a forehead region FH and calculating a forehead area according to the image frame IF, mapping the forehead region FH to the thermal image IT to determine a mapped region $A_{map}$, determining a measured forehead temperature according to a temperature value inside the mapped region $A_{map}$, and compensating or calibrating the measured forehead temperature using the method mentioned below.

The mapping of the forehead region FH is illustrated by examples below.

In one example, the thermal image IT is interpolated to form an interpolated thermal image having the same number of pixels as the image frame IF, and a corresponding mapped region $A_{map}$ in the interpolated thermal image is obtained by overlapping the image frame IF on the interpolated thermal image.

In another example, one pixel of the thermal image IT (e.g., one rectangle in FIG. 2) is corresponded to multiple pixels of the image frame IF, e.g., based on the assumption above one pixel of the thermal image IT corresponding to 30×30 pixels of the image frame IF, and thus it is able to obtain the mapped region $A_{map}$ in the thermal image IT. Based on this assumption, if the mapped region $A_{map}$ includes one pixel of the thermal image IT, the mapped region $A_{map}$ covers corresponding 30×30 pixels of the image frame IF, and so on.

In one aspect, the measured forehead temperature is the maximum temperature inside the mapped region $A_{map}$ of the thermal image IT, but the present disclosure is not limited thereto. In another aspect, the measured forehead temperature is an average of multiple measured temperature values inside the mapped region $A_{map}$ of the thermal image IT. One pixel of the thermal image IT detects one measured temperature value.

To improve the measurement accuracy, the forehead temperature measurement system 100 of the present disclosure further calibrates or compensates the measured forehead temperature. That is, the measured temperature value of a pixel outside the mapped region $A_{map}$ of the thermal image IT is not used as the measured forehead temperature but is used to compensate or calibrate the measured forehead temperature.

Figure 3:
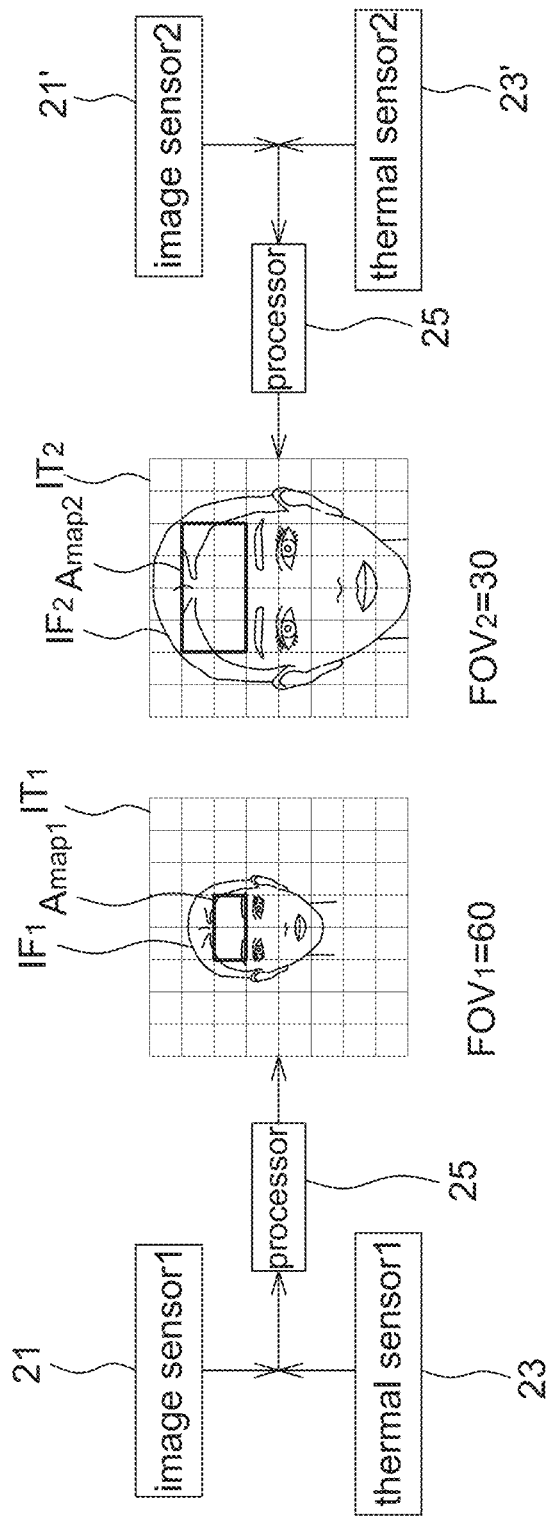
FIG. 3 is a schematic diagram of the temperature measuring of a forehead temperature measurement system according to one embodiment of the present disclosure.

Please refer to FIG. 3, it is a schematic diagram of the temperature measuring of a forehead temperature measurement system 100 according to one embodiment of the present disclosure. In this embodiment, in addition to the image sensor (or referred to first image sensor) 21 and the thermal sensor (or referred to first thermal sensor) 23, the forehead temperature measurement system 100 further includes an image sensor (or referred to second image sensor) 21' and a thermal sensor (or referred to second thermal sensor) 23', wherein the second image sensor 21' and the second thermal sensor 23' are also coupled to the processor 25.

It should be mentioned that although FIG. 3 shows two processors 25, they are only intended to illustrate the operation of two conditions (or modes). The temperature measurement system 100 uses one processor 25 to execute all functions as mentioned above.

In one aspect, the first image sensor 21 and the first thermal sensor 23 have a first field of view, e.g., $FOV_1=60$. The second image sensor 21' and the second thermal sensor 23' have a second field of view, e.g., $FOV_2=30$.

The first image sensor 21 outputs a first image frame $IF_1$, e.g., shown by a human face image when $FOV_1=60$. The first thermal sensor 23 outputs a first thermal image $IT_1$, e.g., shown by a pixel array including 8×8 pixels. The second image sensor 21' outputs a second image frame $IF_2$, e.g., shown by a human face image when $FOV_2=30$. The second thermal sensor 23' outputs a second thermal image $IT_2$, e.g., shown by a pixel array including 8×8 pixels. FIG. 3 shows an overlap of the first image frame $IF_1$ and the first thermal image $IT_1$, and an overlap of the second image frame $IF_2$ and the second thermal image $IT_2$, and said overlap is performed by the processor 25.

More specifically, the processor 25 recognizes a first forehead region (e.g., FH as shown in FIG. 2) and calculates a forehead area according to the first image frame IF. When the forehead area is larger than an area threshold (e.g., recorded in a memory), the processor 25 maps the first forehead region FH to the first thermal image $IT_1$ to accordingly determine a measured forehead temperature, including mapping the first forehead region FH to the first thermal image $IT_1$ to determine a first mapped region $A_{map1}$, and then determining the measured forehead temperature according to a temperature value inside the first mapped region $A_{map1}$. As mentioned above, the measured forehead temperature is the maximum temperature or an average temperature inside the first mapped region $A_{map1}$.

When the forehead area is smaller than the area threshold, the processor 25 controls the second image sensor 21' to capture a second image frame $IF_2$, recognizes a second forehead region according to the second image frame $IF_2$, maps the second forehead region to a second thermal image $IT_2$ captured by the second thermal sensor 23' to determine a second mapped region $A_{map2}$, and determines a measured forehead temperature according to a temperature value inside the second mapped region $A_{map2}$.

In FIG. 3, the processor 25 obtains a measured forehead temperature according to the first mapped region $A_{map1}$ or the second mapped region $A_{map2}$ by using the method identical to FIG. 2, only different sets of sensors being used to perform the calculation. In the embodiment of FIG. 3, when a human face image in the first image frame $IF_1$ is too small (e.g., forehead area smaller than area threshold), the measured forehead temperature is determined by using the second image sensor 21' and the second thermal sensor 23'. Because the second image sensor 21' and the second thermal sensor 23' have a smaller FOV, the human face occupies a larger region in the FOV such that higher measurement accuracy is obtained. For example, the processor 25 is arranged not to process the first thermal image $IT_1$ when the forehead area is smaller than the area threshold, but is arranged to determine the measured forehead temperature according to the first image frame $IF_1$ and the first thermal image $IT_1$ only when the forehead area is larger than or equal to the area threshold.

If the processor 25 needs to calibrate the measured forehead temperature calculated from the second image frame $IF_2$ and the second thermal sensor $IT_2$ using the method mentioned below, the processor 25 further calculates a forehead area according to the second image frame $IF_2$ and an environment temperature according to the second thermal sensor $IT_2$.

Figure 4:
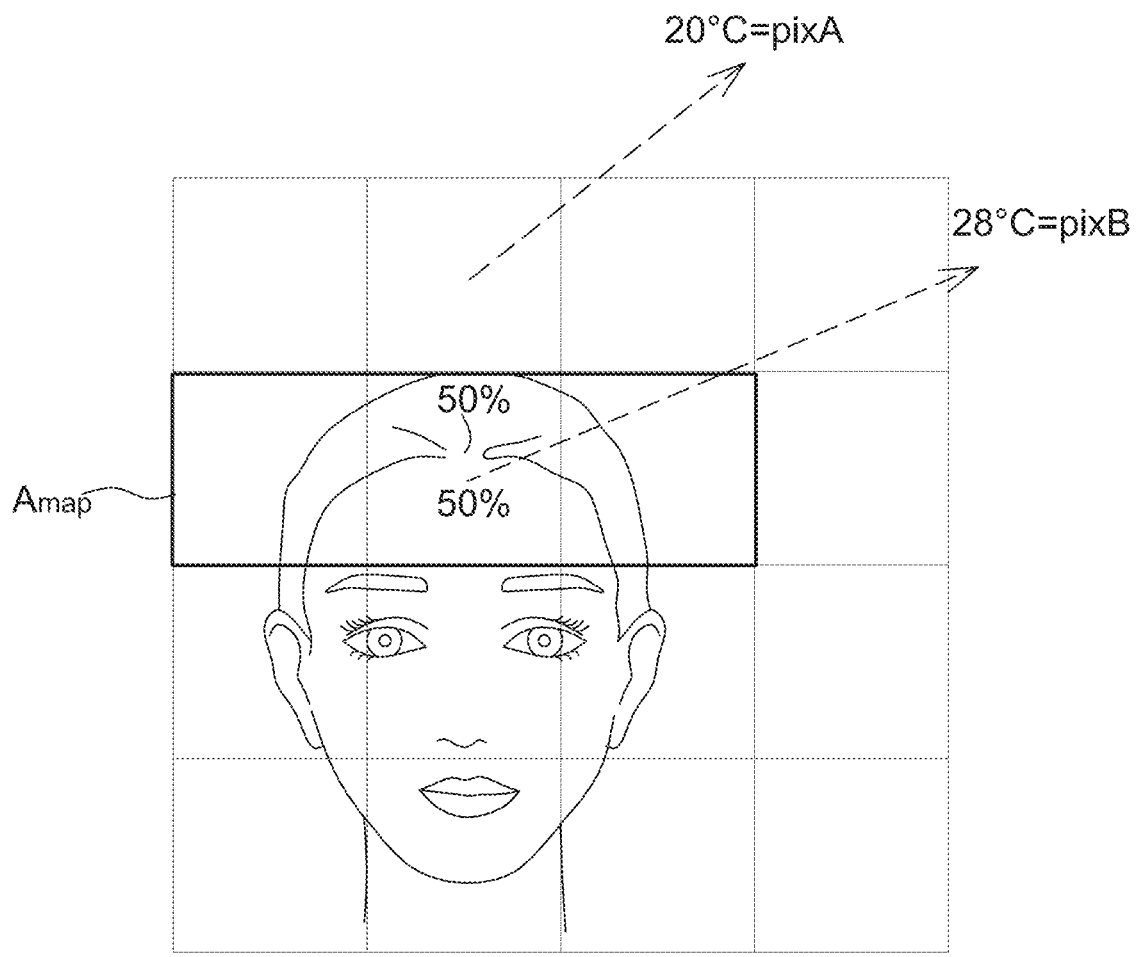
FIG. 4 is another schematic diagram of the temperature measuring of a forehead temperature measurement system according to one embodiment of the present disclosure.

Please refer to FIG. 4, it is another schematic diagram of the temperature measuring of a forehead temperature measurement system 100 according to one embodiment of the present disclosure. Please refer to FIG. 2 together, after receiving the image frame IF and the thermal image IT, the processor 25 recognizes a forehead region FH according to the image frame IF, maps the forehead region FH to the thermal image IT to determine a mapped region $A_{map}$, determines an environment temperature according to a temperature value outside (e.g., pixA in FIG. 4) the mapped region $A_{map}$, finds a pixel of interest (e.g., pixB in FIG. 4) having a maximum temperature inside the mapped region $A_{map}$, recognizes a ratio (e.g., FIG. 4 showing 50% forehead and 50% non-forehead) of the forehead region FH in a corresponding region in the image frame IF corresponding to the pixel of interest pixB, and calculates a measured forehead temperature according to the maximum temperature, the ratio and the environment temperature when the ratio is smaller than a ratio threshold (e.g., 90% to 95% stored in the memory).

In one aspect, the environment temperature is a measured temperature value, e.g., shown as 20° C. in FIG. 4, of a pixel pixA adjacent to the pixel of interest pixB having the maximum temperature (e.g., shown as 28° C. in FIG. 4) in the thermal image IT. The processor 25 recognizes a ratio of forehead region and non-forehead region in a pixel region (e.g., having 30×30 pixels) of the image frame IF corresponding to the pixel of interest pixB. For example, a measured forehead temperature is assumed to be X, and the measured forehead temperature X=36° C. is obtained according to an equation X*50%+20*50%=28. That is, after the ratio of areas of forehead region and non-forehead region, the environment temperature and the maximum temperature are obtained, the corresponding measured forehead temperature is then obtained. In the present disclosure, the measured forehead temperature is not directly equal to the measured temperature value of the pixel of interest.

It is appreciated that the environment temperature is not limited to the measured temperature value of pixA in FIG. 4 but is a measured temperature value of other pixels outside the mapped region $A_{map}$.

However, when the ratio is higher than the ratio threshold, the influence from the environment temperature is considered ignorable, and the processor 25 takes the maximum temperature of the pixel of interest pixB as the measured forehead temperature.

Furthermore, the temperature measuring of FIG. 4 is combinable to the temperature measuring of FIG. 3 (i.e. including two sets of image sensor and thermal sensor). That is, the processor 25 calculates a forehead area according to a first image frame (e.g., $IF_1$ shown in FIG. 3) acquired by the first image sensor 21; and when the forehead area is larger than an area threshold, the processor 25 calculates a measured forehead temperature according to the first image frame $IF_1$ and a thermal image (e.g., $IT_1$ shown in FIG. 3) acquired by the first thermal sensor 23 based on the descriptions of FIG. 4. When the calculated forehead area is smaller than the area threshold, the processor 25 controls the second image sensor 21' to acquire a second image frame (e.g., $IF_2$ shown in FIG. 3) to replace the first image frame $IF_1$ and controls the second thermal sensor 23' to acquire a second thermal image (e.g., $IT_2$ shown in FIG. 3) to replace the first thermal image $IT_1$, and then calculates a measured forehead temperature according to the second image frame $IF_2$ and the second thermal image $IT_2$ based on the descriptions of FIG. 4.

Figure 5:
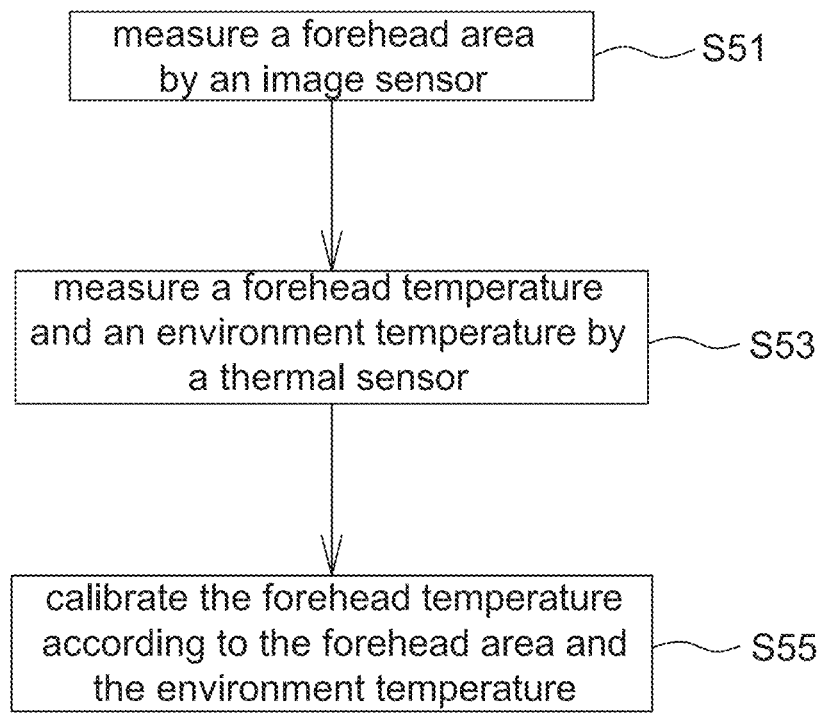
FIG. 5 is a flow chart of a temperature measuring method of a forehead temperature measurement system according to one embodiment of the present disclosure.

Please refer to FIG. 5, it is a flow chart of a temperature measurement method of a forehead temperature measurement system 100 according to one embodiment of the present disclosure, including the steps of: measuring a forehead area using an image sensor (Step S51); measuring a forehead temperature and an environment temperature using a thermal sensor (Step S53); and calibrating the forehead temperature according to the forehead area and the environment temperature (Step S55).

Please refer to FIG. 2 together, one aspect of a temperature measurement method is described below.

Step S51: After receiving the image frame IF, the processor 25 recognizes a forehead region FH in the image frame IF and calculates a forehead area of the forehead region FH. For example, the processor 25 is embedded with an image recognition algorithm (e.g., a model constructed using AI algorithm, but not limited to) for recognizing the forehead region FH. The processor 25 further calculates a number of pixels in the image frame IF occupied by the forehead region FH as a forehead area.

Step S53: After receiving the thermal image IT, the processor 25 then maps the forehead region FH to the thermal image IT to determine a mapped region $A_{map}$ in the thermal image IT. The processor 25 takes a maximum temperature or an average temperature inside the mapped region $A_{map}$ as a measured forehead temperature, and takes a temperature value outside the mapped region $A_{map}$ (e.g., a measured temperature value of a pixel adjacent to the mapped region $A_{map}$ or an averaged measured temperature values of multiple pixels adjacent to the mapped region $A_{map}$) as an environment temperature.

Step S55: Finally, the processor 25 calibrates the measured forehead temperature according to the forehead area and the environment temperature. For example, when the forehead area is smaller, a calibration for calibrating the forehead temperature is larger. For example, when the environment temperature is lower, a calibration for calibrating the forehead temperature is larger. The calibration is, for example, a temperature increment to cause the calibrated forehead temperature to be higher than the measured forehead temperature. In one aspect, when the forehead area is larger than or equal to a predetermined area, the calibration associated with the forehead area is reduced to 0. In another aspect, when the environment temperature is larger than or equal to a predetermined temperature, the calibration associated with the environment temperature is reduced to 0.

Therefore, the forehead temperature measurement system 100 of the present disclosure further includes a memory for previously storing the corresponding relationship between the forehead area and the environment temperature as well as calibrations of the measured forehead temperature such that the processor 25 determines a current calibration according to a current forehead area and a current environment temperature based on the corresponding relationship. The processor 25 then adds the current calibration to a current measured forehead temperature to obtain a calibrated forehead temperature.

In one aspect, before shipment, the forehead temperature measurement system 100 is used to measure a user to calculate measured forehead temperatures under different forehead areas (e.g., corresponding to different distances) and different environment temperatures. Reference temperatures of the same user under the same conditions are obtained by using an accurate temperature sensor (e.g., forehead thermosensor or contact temperature sensor). Then, the forehead area and the environment temperature are used as variables, and the measured forehead temperatures are fitted to the reference temperatures using the fitting method to obtain a fitted equation to be recorded in the memory.

The corresponding relationship is not limited to be obtained using the fitting method as long as the recorded relationship can calibrate the measured forehead temperatures corresponding to different forehead areas and environment temperatures to be close to or even equal to the reference temperatures (i.e. obtaining the calibrations corresponding to different forehead areas and environment temperatures).

Similarly, the embodiment of FIG. 5 is also combinable with the embodiment of FIG. 3. When identifying that the forehead area is smaller than an area threshold, the processor 25 controls the set of sensors having a smaller FOV to perform the forehead temperature measuring. When identifying that the forehead area is larger than or equal to the area threshold, the processor 25 controls the set of sensors having a larger FOV to perform the forehead temperature measuring.

Figure 6:
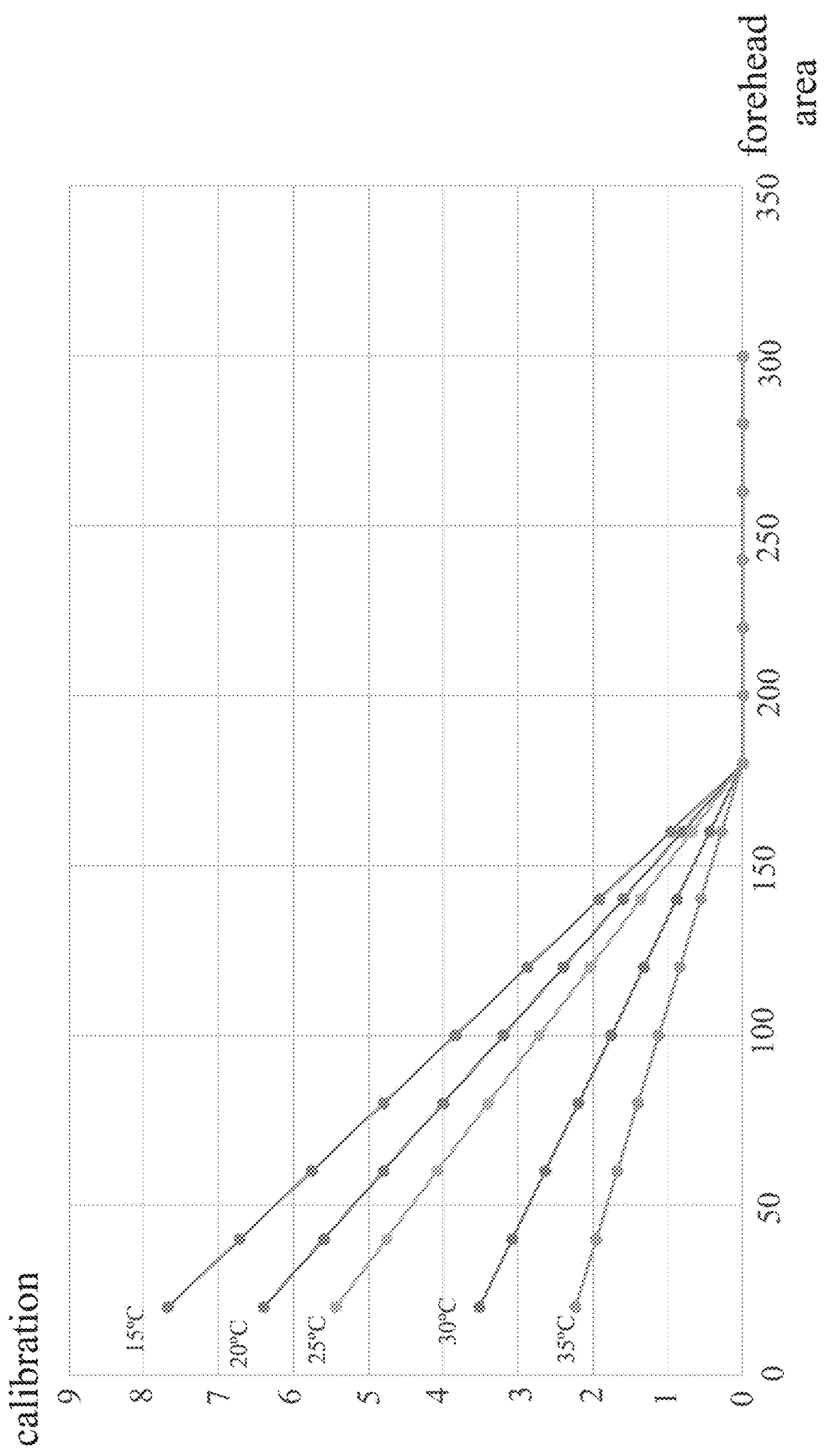
FIG. 6 is a schematic diagram of the temperature compensation of a forehead temperature measurement system according to one embodiment of the present disclosure.

Please refer to FIG. 6, it shows calibrations corresponding to different forehead areas and environment temperatures, wherein a unit of the vertical axis is ° C. When the environment temperature (e.g., shown as 15° C., 20° C., 25° C., 30° C. and 35° C., but not limited to) is lower, the current measured forehead temperature is compensated by a larger calibration corresponding to the same forehead area (e.g., shown as 50, 100, 150, 200, 250 and 300, but not limited to).

Figure 7:
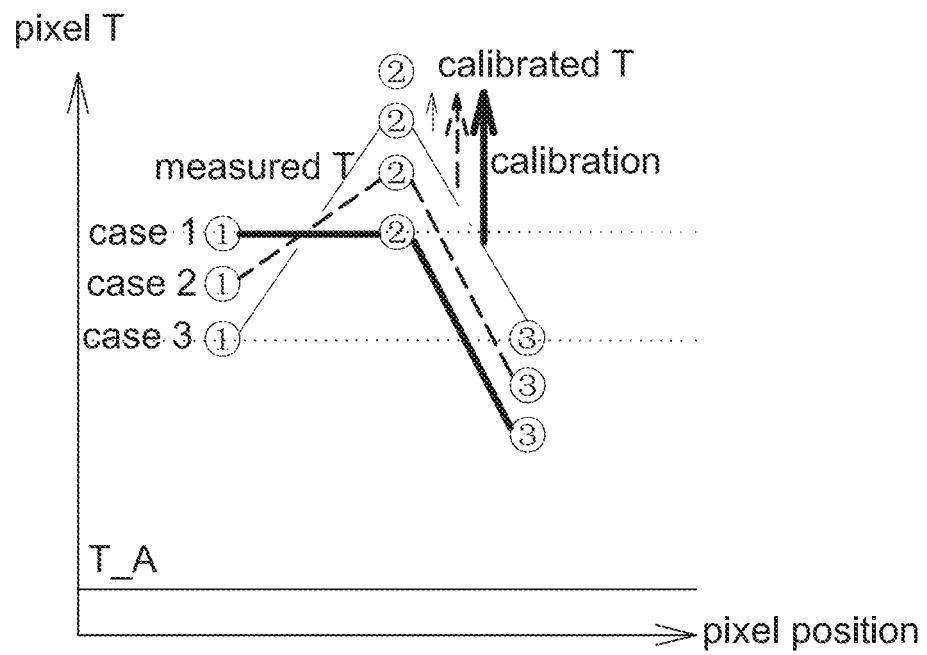
FIG. 7 is a schematic diagram of the temperature compensation of a forehead temperature measurement system according to another embodiment of the present disclosure.

Please refer to FIG. 7, it is a schematic diagram of a temperature measurement method of a forehead temperature measurement system 100 according to one embodiment of the present disclosure, including the steps of: measuring a forehead area using an image sensor; measuring a forehead temperature and adjacent temperatures using a thermal sensor; and calibrating the forehead temperature according to the forehead temperature and the adjacent temperatures.

Please refer to FIG. 2 together, one aspect of a temperature compensation method is described below.

After receiving the image frame IF, the processor 25 recognizes a forehead region FH in the image frame IF and calculates a forehead area of the forehead region FH. For example, the processor 25 is embedded with an image recognition algorithm (e.g., a model constructed using AI algorithm, but not limited to) for recognizing the forehead region FH. The processor 25 further calculates a number of pixels in the image frame IF occupied by the forehead region FH as the forehead area.

After receiving the thermal image IT, the processor 25 then maps the forehead region FH to the thermal image IT to determine a mapped region $A_{map}$ in the thermal image IT. The processor 25 takes a maximum temperature inside the mapped region $A_{map}$ as a measured forehead temperature, and takes temperature values adjacent to a pixel associated with the measured forehead temperature as the adjacent pixels. As shown in FIG. 7, it is assumed that the mapped region $A_{map}$ includes 3 pixels (or 3 pixel regions each including multiple pixels), and a middle pixel (e.g., indicated as ②) outputs the measured forehead temperature and adjacent pixels (e.g., indicated as ① and ③) output adjacent temperatures. It is appreciated that the mapped region $A_{map}$ is not limited to include 3 pixels or pixel regions.

In one aspect, the temperature compensation of this aspect is performed only w % ben the processor 25 identifies that the forehead area is smaller than a predetermined area threshold. When the forehead area is larger than or equal to the predetermined area threshold, the measured forehead temperature is directed outputted without compensation.

Finally, the processor 25 calibrates the measured forehead temperature according to the measured forehead temperature and the adjacent temperatures. For example in a scenario that the mapped region $A_{map}$ includes 3 pixels, the processor 25 firstly calculates a first temperature difference and a second temperature difference between the measured forehead temperature and two adjacent temperatures (e.g., including a first adjacent temperature and a second adjacent temperature), and then calibrates the measured forehead temperature according to uniformity of the first temperature difference and the second temperature difference.

Figure 8A:
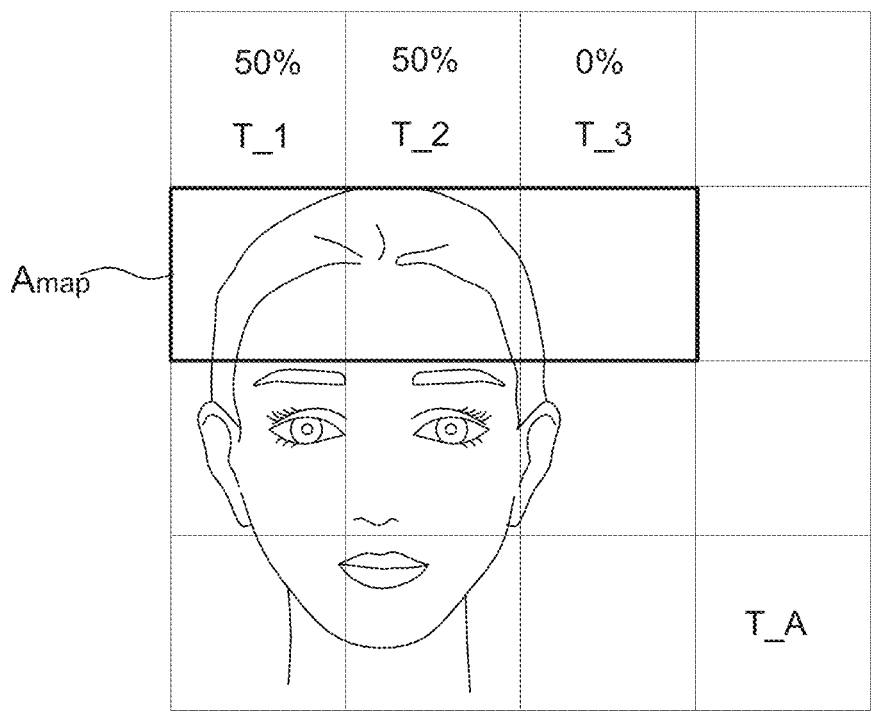
FIGS. 8A to 8C are schematic diagrams of the temperature compensation of FIG. 7.

Please refer to FIGS. 7 and 8A together, the case 1 shows that the measured forehead temperature is T_2, the first adjacent temperature is T_1 and the second adjacent temperature is T_2. In FIG. 8A, a forehead region is mainly corresponding to pixels having T_1 and T_2, and T_1 is substantially identical to T_2. The pixel having T_3 is outside the forehead region and thus has the lowest temperature. In this case, the first temperature difference (T_2−T_1) is substantially identical to 0, and the second temperature difference (T_2−T_3) is large. The uniformity of case 1 is low, and thus the processor 25 determines a larger calibration value.

Figure 8B:
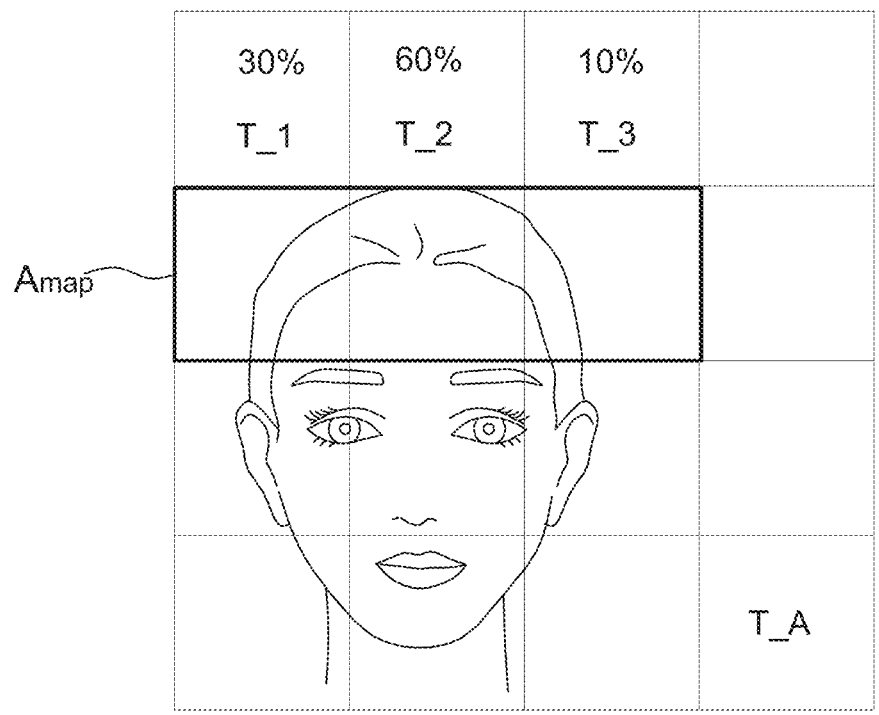

Please refer to FIGS. 7 and 8B together, the case 2 shows that the pixel having T_2 is corresponding to the maximum forehead region (e.g., 60%), and the pixel having T_3 is corresponding to the minimum forehead region (e.g., 10%). In this case, the first temperature difference is smaller than the second temperature difference, which is smaller than the second temperature difference in FIG. 8A. Accordingly, the case 2 has a higher uniformity than case 1, and thus the processor 25 determines a smaller calibration value than case 1.

Figure 8C:
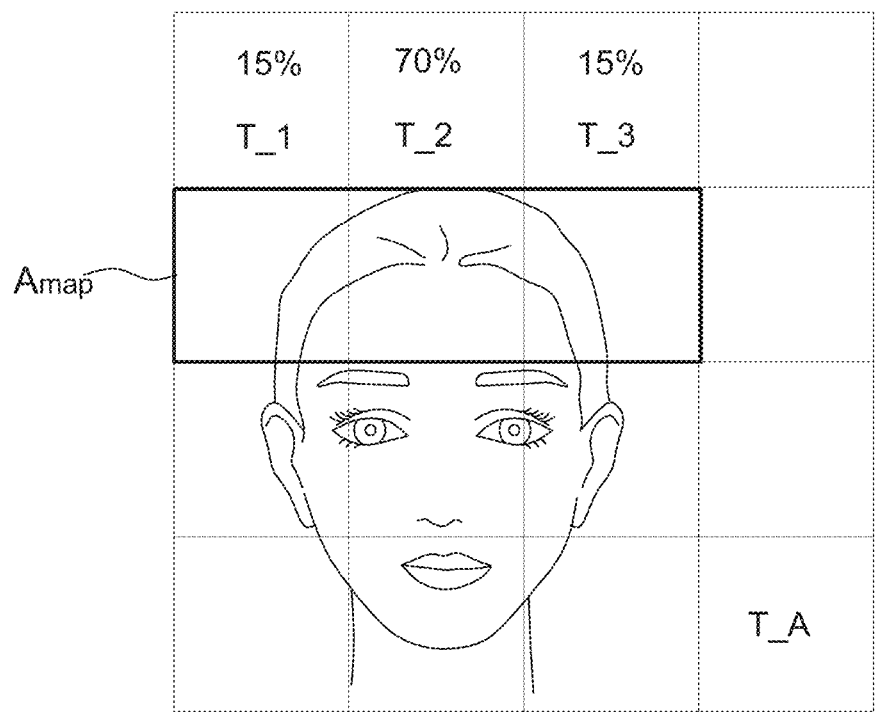

Please refer to FIGS. 7 and 8C together, the case 3 shows that the pixel having T_2 is corresponding to the maximum forehead region (e.g., 70%), and pixels having T_1 and T_3 are corresponding to smaller and identical forehead regions (e.g., 15%). In this case, the first temperature difference is substantially identical to the second temperature difference. The uniformity of case 3 is higher, and thus the processor 25 determines a smaller calibration value.

In other words, if the uniformity is lower (e.g., case 1), the calibration is larger (i.e. more temperature being added to the measured forehead temperature); otherwise, if the uniformity is higher (e.g., case 3), the calibration is smaller (i.e. less temperature being added to the measured forehead temperature).

The forehead temperature measurement system 100 of the present disclosure further includes a memory for previously storing the corresponding relationship between the uniformity and calibrations of the measured forehead temperature such that the processor 25 determines a current calibration according to a current measured forehead temperature and current adjacent temperatures based on the corresponding relationship. The processor 25 then adds the current calibration to the current measured forehead temperature (measured T shown in FIG. 7) to obtain a calibrated forehead temperature (calibrated T shown in FIG. 7).

In one aspect, before shipment, the forehead temperature measurement system 100 is used to measure a user to calculate uniformity under different measured forehead temperatures and adjacent temperatures. Reference temperatures of the same user under the same conditions are obtained by using an accurate temperature sensor (e.g., forehead thermosensor or contact temperature sensor). Then, the measured forehead temperature and the adjacent temperature are used as variables, and the measured forehead temperatures are fitted to the reference temperatures using the fitting method to obtain a fitted equation to be recorded in the memory.

The corresponding relationship is not limited to be obtained using the fitting method as long as the recorded relationship can calibrate the measured forehead temperatures corresponding to different measured forehead temperatures and adjacent temperatures (or uniformity) to be close to or even equal to the reference temperatures (i.e. obtaining the calibrations corresponding to different uniformity).

Similarly, the embodiment of FIG. 7 is also combinable with the embodiment of FIG. 3. When identifying that the forehead area is smaller than an area threshold, the processor 25 controls the set of sensors having a smaller FOV to perform the forehead temperature measuring. When identifying that the forehead area is larger than or equal to the area threshold, the processor 25 controls the set of sensors having a larger FOV to perform the forehead temperature measuring.

Furthermore, the embodiment of FIG. 7 is also combinable with the embodiment of FIG. 5. That is, the processor 25 compensates a measured forehead temperature according to the forehead area, the environment temperature and the distribution of adjacent temperatures in the mapped region $A_{map}$ (e.g., uniformity).

In the present disclosure, the measured forehead temperature or the calibrated forehead temperature is outputted to a display to be shown thereon and/or compared with a temperature threshold to determine whether to generate a warning. For example, the forehead temperature measurement system 100 is arranged to directly output the measured forehead temperature or the calibrated forehead temperature, or to output a flag signal (e.g., outputting digital value 1 when the forehead temperature exceeds 38° C., but not limited to) to indicate that the body temperature is too high.

It should be mentioned that the values mentioned in the above embodiments and drawings, e.g., including temperatures, FOVs, area ratios and pixel numbers are only intended to illustrate but not to limit the present disclosure.

In the present disclosure, the forehead area is, for example, a length, a width or length-width of the forehead region FH.

It should be mentioned that although the above embodiments are illustrated in the way that a forehead area is calculated by the processor 25 according to the image frame IF, e.g., a pixel number of the forehead region FH in the image frame IF, the present disclosure is not limited thereto. In another aspect, the processor 25 calculates the forehead area according to the mapped region $A_{map}$ in the thermal image IT, e.g., a number of pixels of the mapped region $A_{map}$ in the thermal image IT.

As mentioned above, in a temperature measurement system employing a thermal sensor and an image sensor, 2-dimensional images captured by said two sensors are overlapped (e.g., by a processor) at first so as to find measured temperature value(s) in the thermal image corresponding a region of interest (e.g., forehead region) in the image frame. However, the thermal sensor and the image sensor inherently have a position offset in the assembly and, in some cases due to assembling mismatch, further have a viewing angle offset therebetween.

Figure 9:
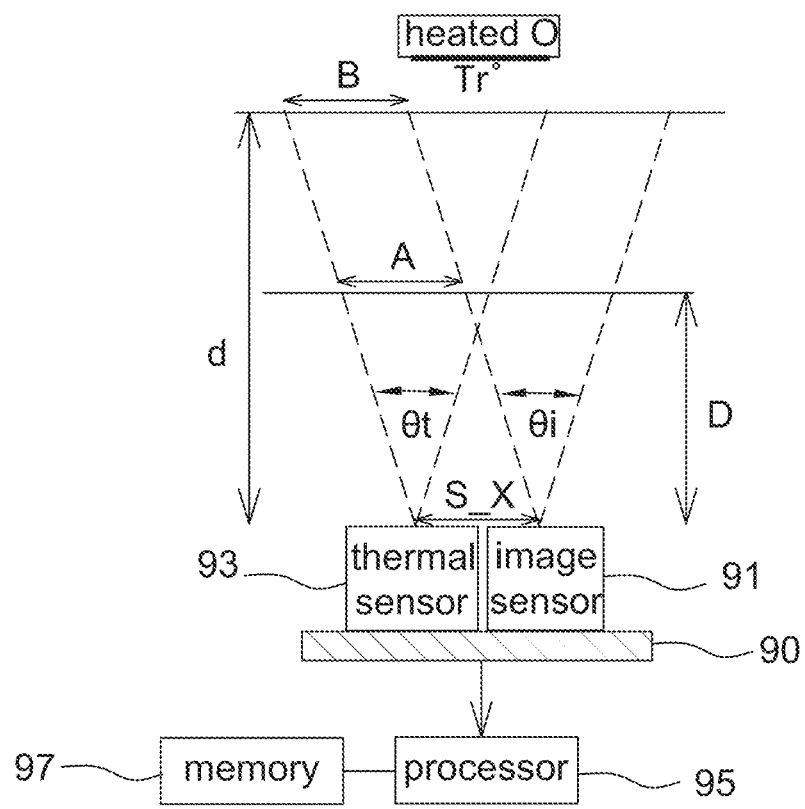
FIG. 9 is a schematic diagram of a position offset between an image sensor and a thermal sensor of a temperature measurement system according to one embodiment of the present disclosure.

For example, referring to FIG. 9, it shows a position offset S_X between an image sensor 91 and a thermal sensor 93 arranged on a circuit board (or substrate) 90, e.g., a PCB or a flexible board. In one aspect, the image sensor 91 is identical to the image sensor 21 mentioned above, and the thermal sensor 93 is identical to the thermal sensor 23 mentioned above. It should be mentioned that although FIG. 9 shows a position offset S_X only in an X direction, it is only intended to illustrate but not to limit the present disclosure. It is appreciated that the image sensor 91 and the thermal sensor 93 may also have a position offset in a Y direction, perpendicular to the X direction.

As shown in FIG. 9, the image sensor 91 captures an image frame IF (referring to FIG. 2 and FIGS. 11A-11B) with a first field of view θi covering a predetermined heated region (e.g., shown as heated O) having a reference temperature Tr°; and the thermal sensor 93 captures a thermal image IT (referring to FIG. 2 and FIGS. 11A-111B) with a second field of view θt covering the predetermined heated region having the reference temperature Tr°.

In one aspect, the predetermined heated region is a black body furnace, but the present disclosure is not limited thereto. The operation and function of the black body furnace is known to the art, e.g., having a heating surface generating the reference temperature Tr°, and thus details thereof are not described herein. In another aspect, the predetermined heated region is selected from other devices or equipment as long as said device/equipment generates a known and accurate reference temperature.

It is seen from FIG. 9 that since there is a position offset S_X (and/or S_Y in another direction) between the image sensor 91 and the thermal sensor 93, the first field of view θi and the second field of view θt (assuming substantially equal to θi and directing to the same direction) also has a position offset, e.g., offset A at a distance D and offset B at a distance B.

Figure 10:
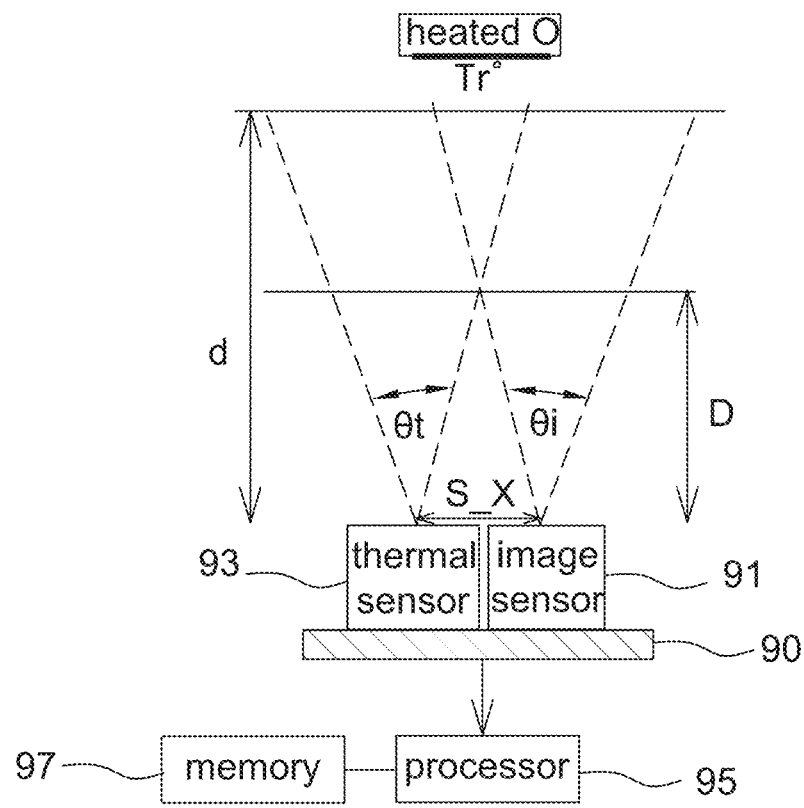
FIG. 10 is a schematic diagram of a position offset and a viewing angle offset between an image sensor and a thermal sensor of a temperature measurement system according to one embodiment of the present disclosure.

For example, referring to FIG. 10, it shows a viewing angle offset as well as a position offset S_X between the image sensor 91 and the thermal sensor 93 arranged on the circuit board 90.

If a temperature measurement system uses the image sensor 91 and the thermal sensor 93 having a position offset S_X as shown in FIG. 9, or having a viewing angle offset as well as a position offset S_X as shown in FIG. 10, a first region of interest (e.g., ROI_1 shown in FIGS. 11A and 11B) in the thermal image IT and a second region of interest (e.g., ROI_2 shown in FIGS. 11A and 11B) in the image frame IF have offset pixels even though the processor 95 (similar to the processor 25 mentioned above) fully overlaps the thermal image IT and the image frame IF. In the present disclosure, both ROI_1 and ROI_2 are associated with the predetermined heated region. It is assumed that ROI_2 is substantially at a central area of the image frame IF, but ROI_1 is deviated from a central area of the thermal image IT due to the position offset and/or the viewing angle offset between the image sensor 91 and the thermal sensor 93.

It should be mentioned that for illustration purposes, the image frame IF is shown to be larger than the thermal image IT. The processor 95 is coupled to the image sensor 91, the thermal sensor 93 and the memory 97.

To improve the accuracy of temperature measurement, the temperature measurement system of the present disclosure includes a memory 97 (e.g., including volatile memory and/or non-volatile memory) which records a calibration temperature before shipment of the temperature measurement system. The recorded calibration temperature is used to calibrate a current temperature (e.g., measured temperature mentioned above) determined according to a current image frame captured by the image sensor 91 and a current thermal image captured by the thermal sensor 93. For example, the method of obtaining a measured temperature is identical to obtaining a measured forehead temperature as mentioned above.

More specifically, the temperature measurement system is operated in a setting mode/stage before shipment so as to record the calibration temperature in the memory 97, and is operated in an operating mode/stage so as to calibrate a measured temperature using the recorded calibration temperature.

Figure 11A:
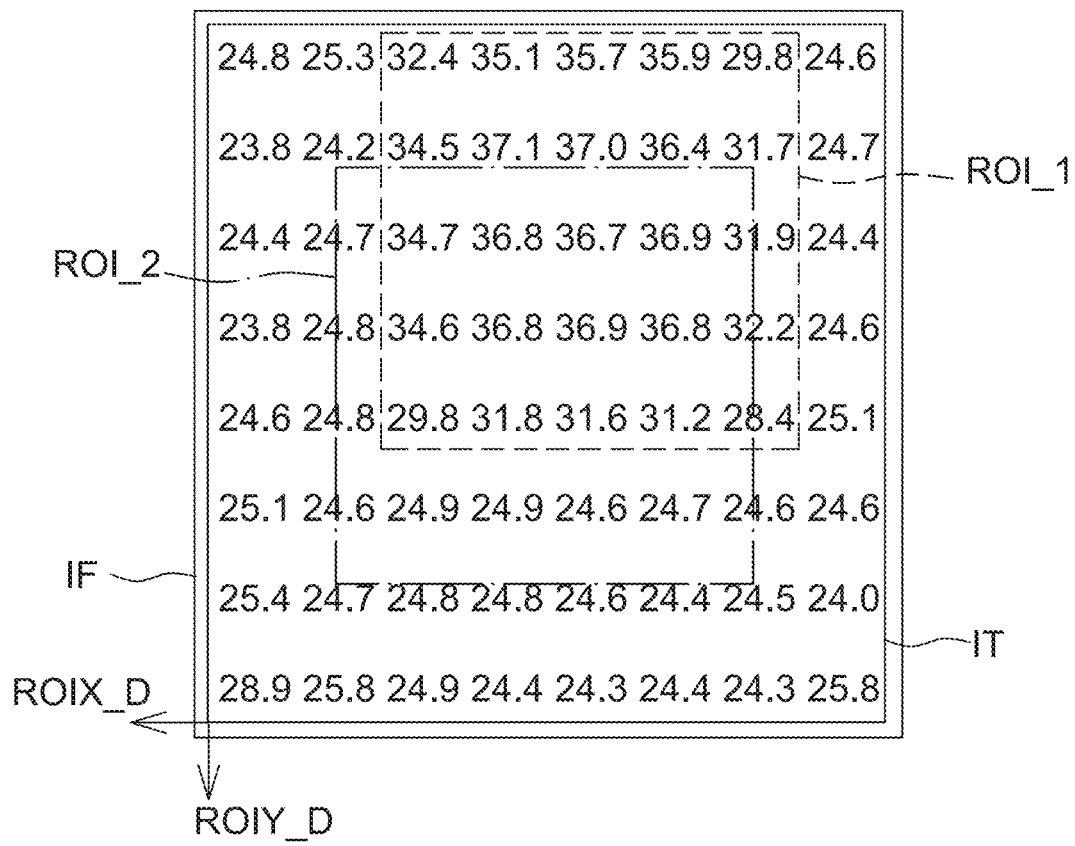
FIG. 11A is a schematic diagram of offset pixels between ROI_2 in an image frame and ROI_1 in a thermal sensor captured by the temperature measurement system of FIG. 9 or 10.
Figure 11B:
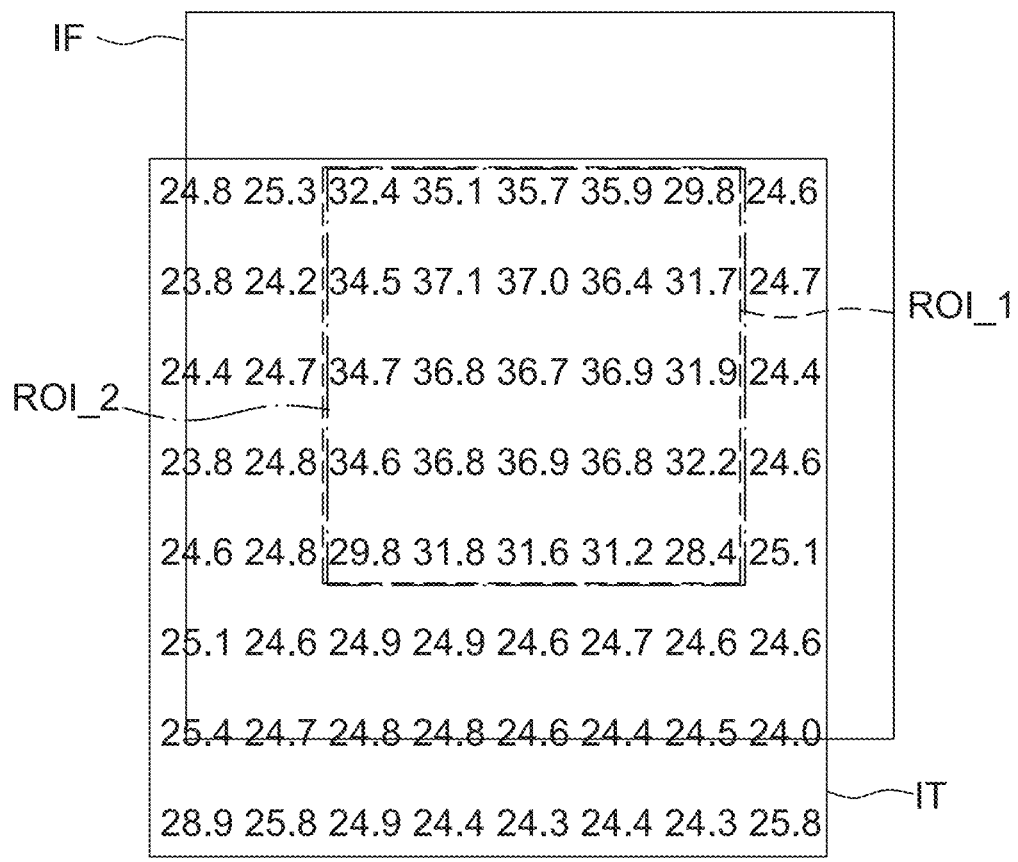
FIG. 11B is a schematic diagram of calibrating the offset pixels in FIG. 11A to cause ROI_1 and ROI_2 to substantially match to each other.

In the present disclosure, the calibration temperature is determined using both the image frame IF captured by the image sensor 91 and the thermal image IT captured by the thermal image 93. In one aspect, the calibration temperature is a temperature difference between the reference temperature Tr° and a measured temperature of a first region of interest ROI_1 associated with the predetermined heated region in the thermal image IT, wherein FIGS. 11A and 11B show 8×8 measured temperatures in the thermal image IT, and ROI_1 covers 5×5 measured temperatures. It is appreciated that a size of ROI_1 is determined according to a size of the heated region, e.g., a heating surface of a black body furnace, as well as the distance D.

It is seen from FIG. 11A that the ROI_1 overlaps at least a part of a second region of interest ROI_2 associated with the predetermined heated region in the image frame IF while overlapping the image frame IF and the thermal image IT. In the setting stage, the processor 95 performs (using predetermined algorithm therein) the overlapping or the overlapping is performed by user operation. In one aspect, before the overlapping, the thermal image IT is interpolated to form an interpolated thermal image having a same number of pixels as the image frame IF. In another aspect, in the overlapping, one pixel of the thermal image IT is corresponded to multiple pixels of the image frame IF. The processor 95 uses any suitable way to overlap the thermal image IT and the image frame IF to cause the thermal image IT and the image frame IF.

In one aspect, the measured temperature is determined without calibrating an offset (caused by mismatch of the image sensor 91 and thermal sensor 93) between ROI_1 and ROI_2 while overlapping the image frame IF and the thermal image IT. As shown in FIG. 11A, the measured temperature is obtained by selecting one measured temperature (e.g., maximum one, but not limited to) or by averaging multiple temperature values within an overlapped region (e.g., a region shown to have 12 temperature values) between ROI_1 and ROI_2.

In another aspect, the measured temperature is determined after calibrating offset pixels between ROI_1 and ROI_2 while overlapping the image frame IF and the thermal image IT. As shown in FIG. 11B, the processor 95 firstly moves at least one of the image frame IF and the thermal image IT (e.g., by ROIX_D in a first direction and/or ROIY_D in a second direction) to cause ROI_1 and ROI_2 to be substantially overlap with each other so as to align ROI_1 associated with the predetermined heated region in the thermal image IT with ROI_2 associated with the predetermined heated region in the image frame IF to calibrate a pixel offset between the first field of view θi and the second field of view θt. The measured temperature is obtained by selecting one measured temperature (e.g., maximum one, but not limited to) or by averaging multiple temperature values within an overlap region (e.g., a region shown to have 25 temperature values, more than FIG. 11A) between ROI_1 and ROI_2. More measured temperatures are averaged in FIG. 11B, which is intended to obtain a more reliable measured temperature.

In addition to record a calibration temperature in the setting mode (or stage), the memory 95 further records a number of offset pixels between the image frame IF and the thermal image IT (more specifically between ROI_2 and ROI_1) captured at a reference distance, e.g., D as shown in FIG. 9.

The offset pixels in FIG. 11A are caused by the position offset S_X and the viewing angle offset shown in FIG. 10. To obtain FIG. 11B from FIG. 11A, the thermal image IT is moved by ROIX_D (e.g., pixel numbers) in a transverse direction and ROIY_D (e.g., pixel numbers) in a longitudinal direction. It is appreciated that it is also possible to move the image frame IF, or move both the image frame IF and the thermal image IT. It is assumed that the image frame IF and the thermal image IT are captured at a reference distance D shown in FIG. 9.

The ROIX_D and ROIY_D are recorded in the memory 95 as the number of offset pixels before shipment of the temperature measurement system. The number of offset pixels includes a first direction offset ROIX_D and a second direction offset ROIY_D, perpendicular to the first direction offset ROIX_D. It is appreciated that if the image sensor 91 and the thermal sensor 93 have the position offset and viewing angle offset only in one direction, the number of offset pixels only in said one direction is previously recorded in the memory 97. In the case that a size of pixel array of the image sensor 91 is 240×240 and the first field of view θi is 60 degrees, the ROIX_D is calculated from 200×S_X/D; and ROIY_D is calculated from 200×S_Y/D. The value "200" is affected by the size of pixel array and the first field of view θi, and is not limited to "200" mentioned herein.

If the temperature measuring system is operated at the reference distance D in operating mode (or stage), a current ROI_1 in the thermal image IT is accurately overlapped with a current ROI_2 (e.g., a forehead region as mentioned in the above embodiments) in the image frame IF after the processor 95 performs the overlapping using the recorded number of offset pixels.

However, in actual operation (i.e. the operating mode/stage), the recorded number of offset pixels is not able to accurately calibrate the position offset at different operating distances.

Figure 12A:
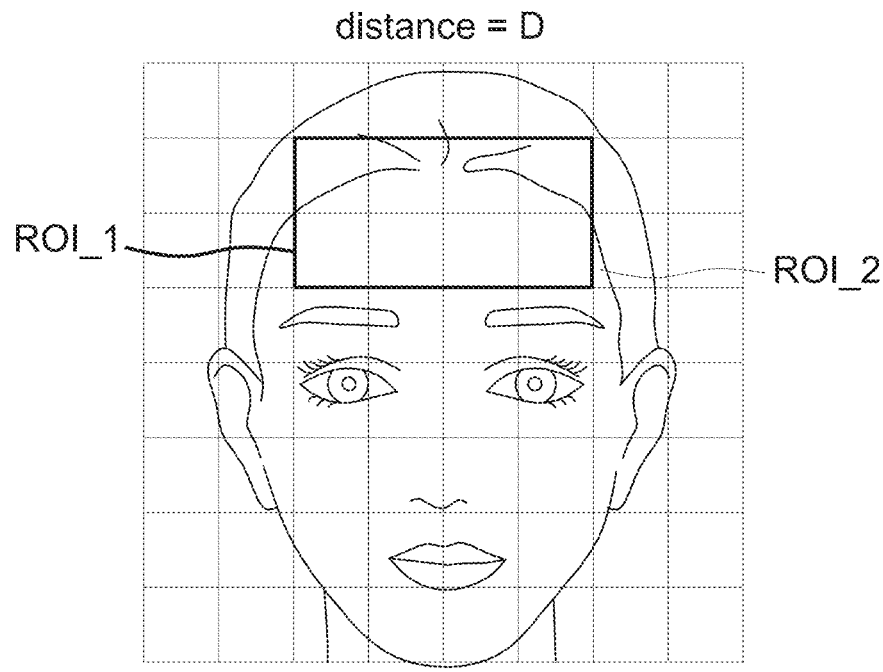
FIGS. 12A and 12B are schematic diagrams of capturing an object at different distances.
Figure 12B:
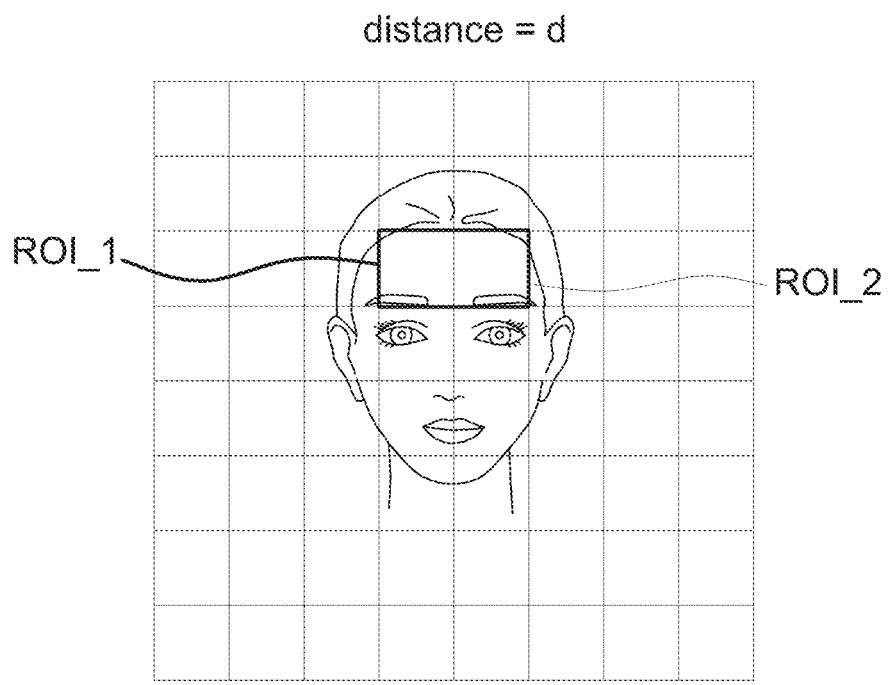

Please refer to FIGS. 12A and 12B, FIG. 12A shows a human face captured at the reference distance D and FIG. 12B shows the same human face captured at an operating distance d. Referring to FIG. 9 together, since d is longer than D, the viewing angle covers larger area at the distance d than at the distance D. If the number of offset pixels recorded based on the reference distance D is directly used to calibrate a pixel offset between ROI_1 and ROI_2 in images captured at a longer distance, a calibrated distance is too much, e.g., one pixel in FIG. 12A covering a larger area than one pixel in FIG. 12B to cause over-calibration.

Therefore, the present disclosure further adjusts the recorded number of offset pixels corresponding to different operating distances, which are determined in operating the temperature measurement system. In one aspect, the operating distance is inputted by a user interface, e.g., coupling the temperature measurement system to a host that runs an APP for the user to enter or select the operating distance. In another aspect, the operating distance is calculated by the processor 95 using the image frame IF, e.g., the processor 95 being embedded with a distance calculation algorithm for the calculation.

In the present disclosure, when the operating distance d is larger than the reference distance D, the number of offset pixels is decreased such that a smaller compensation distance is used in calibrating a position deviation between ROI_1 and ROI_2; whereas when the operating distance d is smaller than the reference distance D, the number of offset pixels is increased such that a larger compensation distance is used in calibrating a position deviation between ROI_1 and ROI_2.

In one aspect, the processor 95 calibrates the number of offset pixels ROIX_D and/or ROIY_D according to a ratio of a difference between an operating distance d and the reference distance D with respect to the operating distance D, e.g., ROIX_D×(d−D)/d and ROIY_D×(d−D)/d. In this way, the recorded number of offset pixels can be used by the processor 95 to calibrate the pixel offset between ROI_1 and ROI_2 at any operating distance d by using the ratio. Meanwhile, the processor 95 further calibrates a current measured temperature of a current first ROI within the thermal image IT using the recorded calibration temperature.

More specifically, the present disclosure provides a calibration method of a temperature measuring system employing an image sensor and a thermal sensor, including the steps of: recording a calibration temperature and a number of offset pixels in a setting mode (Step S131); using the calibration temperature to calibrate a current measured temperature in an operating mode (Step S133); and adjusting the number of offset pixels corresponding to different operating distances and using the adjusted offset pixels to compensate assembling mismatch (Step S135). In the present disclosure, the setting mode is a stage before shipment of the temperature measuring system, and the operating mode is a stage that a user is operating the temperature measuring system.

Step S131: The temperature measuring system is used to capture a heating source, e.g., a black body furnace, but not limited to, at a reference distance D in the setting stage. The image sensor 91 captures an image frame IF; and the thermal sensor 93 captures a thermal image IT, e.g., shown in FIG. 11A. As mentioned above, a calibration temperature is calculated and obtained directly using FIG. 11A or after a number of offset pixels between the image frame IF and the thermal image IT is compensated, as shown in FIG. 11B. Furthermore, the number of offset pixels, e.g., including ROIX_D and/or ROIY_D mentioned above, is recorded in the memory 95 together with the calibration temperature.

Step S133: In operating stage, the temperature measuring system captures a current image frame by the image sensor 91 and a current thermal image by the thermal sensor 93. The processor 95 obtains a current measured temperature of a current ROI_1 within the current thermal image using the method mentioned in the above embodiments (e.g., obtaining measured forehead temperature), and then calibrates the current measured temperature by the calibration temperature, e.g., adding the calibration temperature thereto or subtracting the calibration temperature therefrom. In this way, the initial temperature calibration is done. As mentioned above, the measured temperature is further calibrated according to a distance of an object to be measured, e.g., referring to FIGS. 4 to 8C.

Step S135: If the temperature measuring system is also operated at the reference distance D in the operating stage, the recorded number of offset pixels is directly used to compensate an offset pixel between ROI_1 and ROI_2 as shown in FIG. 11A in overlapping the image frame IF and the thermal image IT. However, if the temperature measuring system is not operated at the reference distance D, the recorded number of offset pixels is adjusted corresponding to different operating distances, e.g., multiplied by a ratio (d−D)/d, and then the adjusted offset pixels are used to compensate the assembling mismatch, including the position offset and viewing angle offset shown in FIG. 10.

More specifically. ROI_1 and ROI_2 are not fully matched by only overlapping the image frame IF and the thermal image IT due to the position offset and the viewing angle offset. Therefore, a number of offset pixels corresponding a reference distance D is previously recorded in the memory 95, and the processor 95 calculates a suitable offset pixels at different operating distances real-timely in actual operation as long as the operating distance is known. After the position offset and viewing angle offset are compensated using the adjusted offset pixels calculated by the processor 95, ROI_1 and ROI_2 are fully overlapped at any operating distance and thus the accuracy of measured temperature is increased.

The processor 95 uses hardware and/or firmware to perform compensation.

Figure 13:
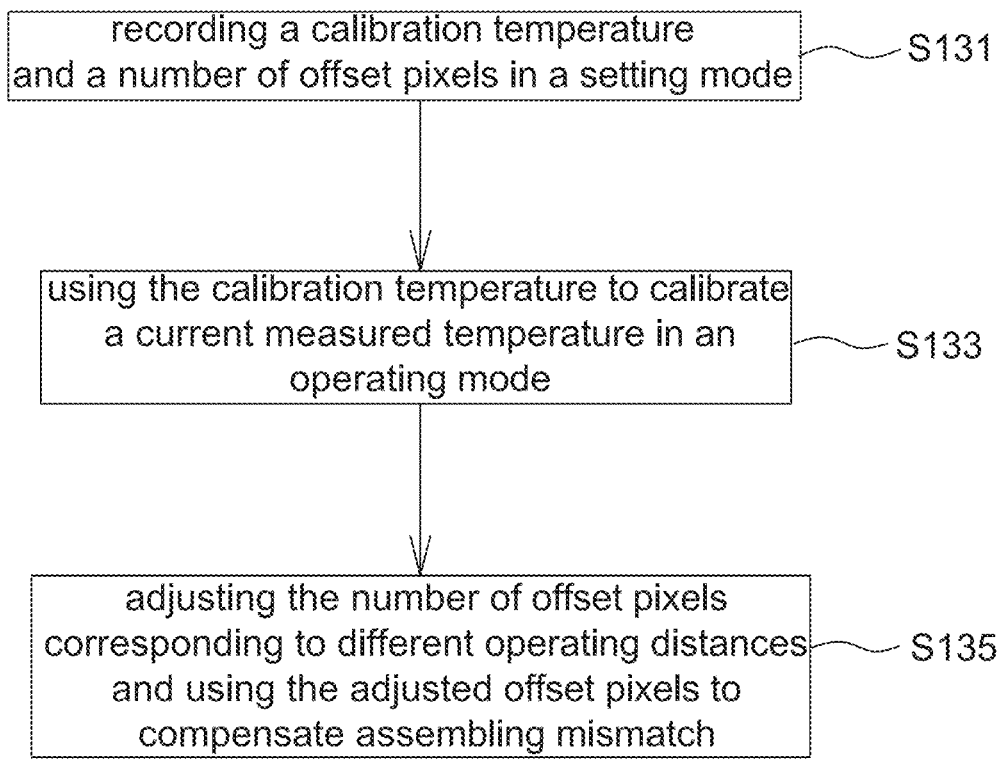
FIG. 13 is a flow chart of a calibration method of a temperature measuring system according to one embodiment of the present disclosure.

A sequence between the Steps S133 and S135 is not limited to that shown in FIG. 13.

The operation of FIG. 13 is combined to the above forehead temperature measuring system to improve the accuracy of temperature measurement. Preferably, the processor compensates the assembly mismatch at first, and then uses the above methods (e.g., from FIG. 2 to FIG. 8C) to calculate the measured temperature.

As mentioned above, the conventional auto forehead temperature measuring system suffers from a temperature deviation caused by the distance of a measured person and the fluctuation of environment temperature. Accordingly, the present disclosure further provides a forehead temperature measurement system capable of compensating or calibrating a measured forehead temperature (e.g., FIGS. 1-4) and a temperature measuring method thereof (e.g., FIG. 5) that firstly confirm a forehead region using an image frame and then determine a measured forehead temperature according to a corresponding region in a thermal region corresponding to the forehead region. Finally, the measured forehead temperature is compensated or calibrated according to a forehead area of the forehead region so as to improve the measurement accuracy.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A temperature measurement system, comprising:
    an image sensor, configured to capture an image frame with a first field of view covering a predetermined heated region having a reference temperature;
    a thermal sensor, configured to capture a thermal image with a second field of view covering the predetermined heated region having the reference temperature; and
    a memory, configured to record a calibration temperature which is a temperature difference between the reference temperature and a measured temperature of a first region of interest (ROI) associated with the predetermined heated region in the thermal image, wherein the first ROI overlaps at least a part of a second ROI associated with the predetermined heated region in the image frame while overlapping the image frame and the thermal image.

2. The temperature measurement system as claimed in claim 1, further comprising a processor configured to calculate an average of multiple temperature values measured within the first ROI as the measured temperature.

3. The temperature measurement system as claimed in claim 1, wherein
    the memory is configured to record the calibration temperature before shipment of the temperature measurement system to calibrate a current temperature determined according to a current image frame captured by the image sensor and a current thermal image captured by the thermal sensor.

4. The temperature measurement system as claimed in claim 1, further comprising a processor configured to determine the measured temperature without calibrating a position offset between the first ROI and the second ROI while overlapping the image frame and the thermal image.

5. The temperature measurement system as claimed in claim 1, further comprising a processor configured to determine the measured temperature after calibrating a position offset between the first ROI and the second ROI while overlapping the image frame and the thermal image.

6. The temperature measurement system as claimed in claim 5, wherein the processor is configured to, before the overlapping, interpolate the thermal image to form an interpolated thermal image having a same number of pixels as the image frame.

7. The temperature measurement system as claimed in claim 5, wherein the processor is configured to cause one pixel of the thermal image to be corresponded to multiple pixels of the image frame in the overlapping.

8. A temperature measurement system, comprising:
    an image sensor, configured to capture an image frame;
    a thermal sensor, configured to capture a thermal image;
    a memory, configured to record a number of offset pixels between the image frame and the thermal image captured at a reference distance; and
    a processor, coupled to the image sensor, the thermal sensor and the memory, and configured to
    calibrate the number of offset pixels according to a ratio of a difference between an operating distance and the reference distance with respect to the operating distance.

9. The temperature measurement system as claimed in claim 8, wherein
    the memory is configured to record the number of offset pixels before shipment of the temperature measurement system, and
    the processor is configured to determine the operating distance in operating the temperature measurement system.

10. The temperature measurement system as claimed in claim 8, further comprising a user interface configured to input the operating distance.

11. The temperature measurement system as claimed in claim 8, wherein the processor is configured to calculate the operating distance using the image frame.

12. The temperature measurement system as claimed in claim 8, wherein
the processor is configured to decrease the number of offset pixels when the operating distance is larger than the reference distance, and
the processor is configured to increase the number of offset pixels when the operating distance is smaller than the reference distance.

13. The temperature measurement system as claimed in claim 8, wherein the number of offset pixels includes a first direction offset and a second direction offset, which is perpendicular to the first direction offset.

14. A temperature measurement system, comprising:
an image sensor, configured to capture an image frame with a first field of view covering a predetermined heated region having a reference temperature;
a thermal sensor, configured to capture a thermal image with a second field of view covering the predetermined heated region having the reference temperature; and
a memory, configured to record
a calibration temperature which is a temperature difference between the reference temperature and a measured temperature of a first region of interest (ROI) associated with the predetermined heated region in the thermal image, wherein the first ROI overlaps at least a part of a second ROI associated with the predetermined heated region in the image frame while overlapping the image frame and the thermal image, and
a number of offset pixels between the image frame and the thermal image captured at a reference distance.

15. The temperature measurement system as claimed in claim 14, further comprising a processor configured to
calibrate the number of offset pixels according to a ratio of a difference between an operating distance and the reference distance with respect to the operating distance, and
calibrate a current measured temperature of a current first ROI within the thermal image.

16. The temperature measurement system as claimed in claim 15, further comprising a user interface configured to input the operating distance.

17. The temperature measurement system as claimed in claim 15,
the processor is configured to decrease the number of offset pixels when the operating distance is larger than the reference distance, and
the processor is configured to increase the number of offset pixels when the operating distance is smaller than the reference distance is increased.

18. The temperature measurement system as claimed in claim 14, further comprising a processor configured to determine the measured temperature after calibrating the number of offset pixels between the image frame and the thermal image captured at the reference distance.

* * * * *